(12) United States Patent
Kataoka et al.

(10) Patent No.: US 7,949,093 B2
(45) Date of Patent: May 24, 2011

(54) X-RAY FLUORESCENCE SPECTROMETER

(75) Inventors: Yoshiyuki Kataoka, Takatsuki (JP);
Hisayuki Kohno, Takatsuki (JP);
Noboru Yamashita, Takatsuki (JP);
Makoto Doi, Takatsuki (JP)

(73) Assignee: Rigaku Industrial Corporation, Tokyo (JP)

( * ) Notice: Subject to any disclaimer, the term of this patent is extended or adjusted under 35 U.S.C. 154(b) by 91 days.

(21) Appl. No.: 12/296,383

(22) PCT Filed: Nov. 24, 2006

(86) PCT No.: PCT/JP2006/323407
§ 371 (c)(1),
(2), (4) Date: Oct. 7, 2008

(87) PCT Pub. No.: WO2007/116559
PCT Pub. Date: Oct. 18, 2007

(65) Prior Publication Data
US 2009/0116613 A1    May 7, 2009

(30) Foreign Application Priority Data

Apr. 11, 2006  (JP) ................................. 2006-108491

(51) Int. Cl.
*G01N 23/223*    (2006.01)
(52) U.S. Cl. ........................................................ 378/45
(58) Field of Classification Search .................. 378/44, 378/45, 47, 50
See application file for complete search history.

(56) References Cited

U.S. PATENT DOCUMENTS

| 2,924,715 | A | * | 2/1960 | Hendee et al. ............... 378/49 |
| 4,134,012 | A | | 1/1979 | Smallbone et al. |
| 4,870,281 | A | | 9/1989 | Van Der Borst et al. |
| 5,598,451 | A | * | 1/1997 | Ohno et al. ................... 378/44 |
| 6,668,038 | B2 | * | 12/2003 | Kataoka et al. .............. 378/45 |

FOREIGN PATENT DOCUMENTS

| JP | 02-003941 B2 | 1/1990 |
| JP | 08-136480 A | 5/1996 |
| JP | 2003-344544 A | 12/2003 |
| JP | 2006-030018 A | 2/2006 |

OTHER PUBLICATIONS

Translation for JP 2006-030018 published Feb. 2, 2006.*
Translation for JP 2003-344544 published Dec. 3, 2003.*
Barlow, et al., "Rapid determination of sulphate for cement mill control," World Cement, Apr. 1986, p. 91-93, vol. 17, No. 3.
Bearden, "X-Ray Wavelengths," Reviews of Modern Physics, Jan. 1967, p. 78-124, vol. 39, No. 1.
Korean Office Action issued in Korean Application No. 10-2008-7027449 dated Dec. 28, 2010.

* cited by examiner

*Primary Examiner* — Chih-Cheng G Kao
(74) *Attorney, Agent, or Firm* — Sughrue Mion, PLLC

(57) ABSTRACT

An X-ray fluorescence spectrometer for measuring the concentration of sulfur contained in a sample (S), by irradiating the sample (S) with primary X-rays from an X-ray tube (11), monochromating fluorescent X-rays emitted from the sample (S) with a spectroscopic device, and detecting monochromated fluorescent X-rays with an X-ray detector. The spectrometer includes the X-ray tube (11) having a target with an element including chromium, an X-ray filter (13) disposed on a path of travel of X-rays between the X-ray tube (11) and the sample (S) and having a predetermined transmittance for Cr—Kα line from the X-ray tube (11) and made of a material which is an element of which absorption edges do not exist between energies of S—Kα line and Cr—Kα line, and a proportional counter (18) having a detector gas containing a neon gas or a helium gas.

4 Claims, 6 Drawing Sheets

X-RAY FLUORESCENCE SPECTROMETER

BACKGROUND OF THE INVENTION

The present invention relates to an X-ray fluorescence spectrometer for analyzing sulfur contained in a sample.

The concentration of sulfur contained in fuel oil such as, for example, gasoline, diesel oil or kerosene has its uppermost limit determined by the standards and is, accordingly, measured during or after refinement of the crude oil for administrative or control purpose. In recent years, regulations have become tighter not only in Japan, but also in the United States and European countries and the uppermost limit in the relevant standards has come to be lowered, accompanied by the requirement to analyze even a very small quantity, say, 5 ppm or smaller, of sulfur.

The X-ray fluorescence analysis has hitherto been employed to analyze the sulfur concentration in the fuel oil such as, for example, gasoline, diesel oil or kerosene, but is incapable of providing a sufficient precision of analysis and the lower limit of detection at a concentration lower than the uppermost limit determined by the current standards.

As the conventional X-ray fluorescence spectrometer for analyzing sulfur contained in the fuel oil such as, for example, gasoline, diesel oil or kerosene, which has hitherto been utilized, an X-ray fluorescence spectrometer, including an X-ray tube having a titanium target, a titanium foil filter, and an X-ray fluorescence spectrometer including an X-ray tube having a scandium target and a scandium foil filter, and an X-ray fluorescence spectrometer including an X-ray tube having a scandium target and a titanium foil filter are known. (See the Patent Document 1 below.)

The X-ray fluorescence spectrometer 6 disclosed in the Patent Document 1 is an energy dispersive X-ray fluorescence spectrometer which is, as shown in FIG. 6, so designed that primary X-rays 62 emitted from an X-ray tube 61 having a titanium target are, after having been filtered through a titanium foil filter 63, irradiated to a sample S and fluorescent X-rays 65 emitted from the sample S are measured by a semiconductor detector 68 without being monochromated by any spectroscopic device.

While the primary X-rays 62 before being filtered through the titanium foil filter 63 contain a substantial amount of continuous X-rays together with Ti—K$\alpha$ lines, the primary X-rays 62 after having been filtered through the titanium foil filter have such an X-ray spectrum as shown in FIG. 8, in which continuous X-rays are appreciably cut off. However, the continuous X-rays are not completely cut off and the remaining continuous X-rays are irradiated to the sample S, causing the latter to generate scattered X-rays which form a considerable background. With the semiconductor detector 68, the energy resolution, that is, sufficient separation of the wavelengths cannot be achieved, and, therefore, the background cannot be sufficiently minimized in comparison with S—K$\alpha$ line, which are fluorescent X-rays representative of sulfur that have been emitted from the sample. For this reason, the background, when converted into the concentration of sulfur, is as large as 100 ppm and the precision of analysis for a very small amount of sulfur is in no way sufficient to accommodate the recent standard value.

Even the X-ray fluorescent spectrometer including the X-ray tube having the scandium target and the scandium foil filter, and the X-ray fluorescent spectrometer including the X-ray tube having the scandium target and the titanium foil filter, which are the X-ray fluorescence spectrometers disclosed in the Patent Document 1 below, have problems similar to that discussed above and accordingly the energy dispersive X-ray fluorescent spectrometer is incapable of achieving the lower limit of detection and a sufficiently precision even though it makes use of an X-ray tube, having a target suitable to analysis of sulfur, and a primary beam filter.

Also, a wavelength dispersive X-ray fluorescent spectrometer is known, which includes, as shown in FIG. 9, an X-ray tube 91 having a target of rhodium (Rh) capable of generating Rh—L$\alpha$ lines (2.70 keV) or palladium (Pd) capable of generating Pd—L$\alpha$ lines (2.84 keV), which are characteristic X-rays having an excellent excitation efficiency to S—K$\alpha$ line (2.31 keV), which are fluorescent X-ray line of sulfur, in the vicinity of the absorption edge wavelength of sulfur, and a proportional counter 98 utilizing argon gas as a detector gas.

Since this X-ray fluorescence spectrometer 9 does not make use of a primary beam filter disposed on a portion of the path of travel of the X-rays between the X-ray tube 91 and the sample S, the sample S is irradiated with primary X-rays 92 containing a substantial amount of continuous X-rays generated from the X-ray tube 91 and the fluorescent X-rays 97, which have been monochromated by a graphite spectroscopic device 96 to measure the fluorescent X-rays 95 emitted from the sample S, are measured with the proportional counter which is an X-ray detector, but scattered X-rays generated by the continuous X-rays are generated in a substantial quantity and, accordingly, the spectroscopic device 96 is incapable of sufficiently minimizing the background of the S—K$\alpha$ line, which are analytical lines of sulfur.

If a primary beam filter in the form of an aluminum foil of 12 $\mu$m in thickness is disposed on a portion of the path of travel of the X-rays between the X-ray tube 21 of the conventional X-ray fluorescence spectrometer 9 and the sample S, the transmittance for the X-rays with the energy of S—K$\alpha$ line, which form the background of the S—K$\alpha$ line, will be 0.6%, but the transmittance of the Ph—L$\alpha$ line and the Pd—L$\alpha$ line from the X-ray tube 91, which is a source of excitation of the fluorescent X-rays of sulfur, is 5% or lower and, accordingly, the efficiency of excitation of the sulfur is extremely low and the sulfur, which is an element to be analyzed, cannot be sufficiently excited, making it difficult to achieve the analysis with high sensitivity.

While the conventional wavelength dispersive X-ray fluorescence spectrometer 9 is so designed that the fluorescent X-rays 95 emitted from the sample S are monochromated by the spectroscopic device 96 to select the X-rays of S—K$\alpha$ line, which are in turn detected by the proportional counter 98, the X-rays diffracted by the spectroscopic device 96 are not only first order line of S—K$\alpha$ line having an energy of 2.31 keV, but also second order line having an energy of 4.62 keV, and then both diffracted X-rays are incident on the proportional counter 98.

At this time, the X-rays of an energy of 4.62 keV included in the scattered X-rays generated as a result of irradiation of the continuous X-rays from the X-ray tube 91 upon the sample are also diffracted by the spectroscopic device 96 and are incident on the proportional counter 98. When the X-rays of 4.62 keV are incident on the proportional counter 98 having argon gas, the energy of the X-rays is lost by 3.0 keV, which is the energy of Ar—K$\alpha$ line, due to the argon contained in the proportional counter 98, resulting in appearance of an escape peak of 1.62 keV. This escape peak is equivalent to 70% of the energy of the S—K$\alpha$ line, which is analytical line of sulfur and cannot be separated by a pulse height analyzer 99 from the S—K$\alpha$ line, thus constituting a large background.

It has been well understood that the fluorescent X-rays from the sample are incident on the proportional counter and the argon gas, which is a gas in the detector, exhibits an escape peak at the value of energy, which is lower than the incident fluorescent X-rays by an energy of the Ar—Kα line and the fluorescent X-rays of higher order lines such as second order line form interfering lines to the analytical lines. By way of example, Co—Kα third order line interferes the S—Kα lines. However, it has not yet been understood that the higher order lines such as the second order line of the continuous X-rays diffracted by the spectroscopic device result in an escape peak and this forms a background, resulting in error in analysis and deterioration in analytical precision, and this phenomenon has now been discovered. Accordingly, to remove the interference of the higher order lines of the continuous X-rays has not been attempted before.

As discussed above, with the conventional wavelength dispersive X-ray fluorescent spectrometer, sulfur cannot be sufficiently excited if the primary beam filter such as, for example, an aluminum foil is used, and a quantitative analysis of a very small amount of sulfur contained in the fuel oil has been considered difficult to achieve. Also, the second order line of the scattered X-ray of the continuous X-rays from the X-ray tube causes an escape peak attributable to the argon gas in the proportional counter, which in turn interfere the S—Kα line, which is analytical line of sulfur, to thereby form a large background, making it difficult to analyze a very small amount of sulfur with high precision. Also, since the background is high, variation of the background among samples adversely affects the analytical values, resulting in an analytical errors.

[Patent Document 1] JP Laid-open Patent Publication No. H08-136480

SUMMARY OF THE INVENTION

The present invention has been devised in view of the foregoing problems and inconveniences discussed above and is intended to provide an X-ray fluorescence spectrometer for analyzing sulfur contained in a sample, in which the scattered X-rays from the sample, which are brought about by continuous X-rays from the X-ray tube, and the escape peak resulting from the detector gas are reduced considerably to improve the lower limit of detection, the precision of analysis of the concentration of a very small amount and the ratio between the peak and the background.

In order to accomplish the foregoing object, the X-ray fluorescence spectrometer according to a first aspect of the present invention is an X-ray fluorescence spectrometer for measuring the concentration of sulfur contained in a sample, by irradiating the sample with primary X-rays from an X-ray tube, monochromating fluorescent X-rays emitted from the sample with a spectroscopic device, and detecting monochromated fluorescent X-rays with an X-ray detector, which spectrometer includes the X-ray tube having a target with an element including chromium, an X-ray filter disposed on the path of travel of X-rays between the X-ray tube and the sample and having a predetermined transmittance for Cr—Kα line generated from the X-ray tube, and a proportional counter having a detector gas including neon gas or helium gas.

According to the first aspect of the present invention, since the provision is made of the X-ray tube capable of generating Cr—Kα line having a higher energy than the exciting energy of S—Kα line, which is the analytical line of sulfur, and the X-ray filter operable to sufficiently transmit the Cr—Kα line and to sufficiently remove continuous X-rays corresponding to the energy of the S—Kα line from the X-ray tube having the target with an element including chromium, sulfur contained in the sample can be sufficiently excited and scattered X-rays resulting from the continuous X-rays and generated from the sample can be suppressed considerably. Also, since the provision is made of the proportional counter having the detector gas containing neon or helium, the background intensity can be minimized by removing influences brought about by an escape peak of second order line at the wavelength of the S—Kα line which is the analytical line of sulfur. Accordingly, the lower limit of detection and the precision of analysis for a very small amount concentration can be improved considerably.

In the practice of the first aspect of the present invention, the target of the X-ray tube may be made of a chromium metal or an alloy of a chromium metal and any other metal. The X-ray filter may be of any type provided that it has, for example, a 50% or higher transmittance for the Cr—Kα line and may have a thickness appropriate to a material such as, for example, aluminum, iron or vanadium foil of which absorption edges do not exist between energies of Cr—Kα lines and S—Kα lines which are analytical lines of sulfur. The proportional counter may be either a sealed proportional counter or a gas flow proportional counter, but the use of the sealed proportional counter is preferred particularly in the case of a compact X-ray fluorescence spectrometer. The detector gas may be either a neon gas or a helium gas. For a quenching gas that is mixed with the detector gas in a predetermined mixing ratio is preferably a carbon dioxide gas.

Table 1 below illustrates examples of counting efficiencies (%) of detector gases for the first order line at S—Kα line and the second order line at S—Kα line. As shown in Table 1, the counting efficiency of the second order line for each of the neon gas and the helium gas is about ⅕ relative to the first order line at S—Kα line. Also, the escape peak of the neon gas corresponds to an energy of about 160% of the first order line at S—Kα line and influences brought about by the escape peak can be removed by a pulse height analyzer. Also, with the helium gas, since no escape peak appear, the second order line can be removed by a pulse height analyzer.

TABLE 1

| Detector Gas | Argon Gas | Neon Gas | Helium Gas |
|---|---|---|---|
| First Order Line at S-Kα Line | 67 | 54 | 57 |
| Second Order Line at S-Kα Line | 76 | 14 | 13 |

The X-ray fluorescence spectrometer according to a second aspect of the present invention is an X-ray fluorescence spectrometer for measuring the concentration of sulfur contained in a sample, by irradiating the sample with primary X-rays from an X-ray tube, monochromating fluorescent X-rays emitted from the sample with a spectroscopic device, and detecting monochromated fluorescent X-rays with an X-ray detector, which spectrometer includes the X-ray tube having a target with an element including titanium, an X-ray filter disposed on a path of travel of X-rays between the X-ray tube and the sample and having a predetermined transmittance for Ti—Kα line from the X-ray tube and made of a material which is an element of which absorption edge do not exist between energies of S—Kα line and Ti—Kα line, and a proportional counter having a detector gas containing a neon gas or a helium gas.

According to the second aspect of the present invention, since the provision is made of the X-ray tube capable of generating Ti—Kα line having a higher energy than the exciting energy of S—Kα line, which is the analytical line of sulfur, and the X-ray filter operable to sufficiently transmit the Ti—Kα line and to sufficiently remove continuous X-rays corresponding to an energy of the S—Kα lines from the X-ray tube having the target with an element including chromium, sulfur contained in the sample can be sufficiently excited and scattered X-rays resulting from the continuous X-rays and generated from the sample can be suppressed considerably. Also, since the provision is made of the proportional counter having the detector gas containing neon or helium, the background intensity can be minimized by removing influences brought about by an escape peak of second order line at the wavelength of the S—Kα line which is the analytical line of sulfur. Accordingly, the lower limit of detection and the precision of analysis for a very small amount concentration can be improved considerably.

In the practice of the second aspect of the present invention, the target of the X-ray tube may be made of a titanium metal or an alloy of a titanium metal and any other metal. The X-ray filter may be of any type provided that it has, for example, a 40% or higher transmittance relative to the Ti—Kα line and may have a thickness appropriate to a material such as, for example, aluminum, iron, titanium or vanadium foil of which absorption edges do not exist between energies of Ti—Kα line and S—Kα line which is analytical line of sulfur. The proportional counter is preferably of a type that is employed in the practice of the first aspect of the present invention.

The X-ray fluorescence spectrometer according to a third aspect of the present invention is an X-ray fluorescence spectrometer for measuring the concentration of sulfur contained in a sample, by irradiating the sample with primary X-rays from an X-ray tube, monochromating fluorescent X-rays emitted from the sample with a spectroscopic device, and detecting monochromated fluorescent X-rays with an X-ray detector, which spectrometer includes the X-ray tube having a target with an element including scandium, an X-ray filter disposed on a path of travel of X-rays between the X-ray tube and the sample and having a predetermined transmittance for Sc—Kα line from the X-ray tube and made of a material which is an element of which absorption edges do not exist between energies of S—Kα line and Sc—Kα line, and a proportional counter having a detector gas containing a neon gas or a helium gas.

According to the third aspect of the present invention, since the provision is made of the X-ray tube capable of generating Sc—Kα lines having a higher energy than the exciting energy of S—Kα line, which is the analytical line of sulfur, and the X-ray filter operable to sufficiently transmit the Sc—Kα lines and to sufficiently remove continuous X-rays corresponding to an energy of the S—Kα lines from the X-ray tube having the target with an element including chromium, sulfur contained in the sample can be sufficiently excited and scattered X-rays resulting from the continuous X-rays and generated from the sample can be suppressed considerably. Also, since the provision is made of the proportional counter having the detector gas containing neon or helium, the background intensity can be minimized by removing influences brought about by an escape peak of second order line at the wavelength of the S—Kα line which is the analytical line of sulfur. Accordingly, the lower limit of detection and the precision of analysis of a very small amount concentration can be improved considerably.

In the practice of the third aspect of the present invention, the target of the X-ray tube may be made of a scandium metal. The X-ray filter may be of any type provided that it has, for example, a 40% or higher transmittance for the Sc—Kα line and may have a thickness appropriate to a material such as, for example, aluminum, iron, titanium or scandium foil of which absorption edges do not exist between energies of Sc—Kα line and S—Kα line which is the analytical lines of sulfur. The proportional counter is preferably of a type that is employed in the practice of the first aspect of the present invention.

The X-ray fluorescence spectrometer according to a fourth aspect of the present invention is an X-ray fluorescence spectrometer for measuring the concentration of sulfur contained in a sample, by irradiating the sample with primary X-rays from an X-ray tube, monochromating fluorescent X-rays emitted from the sample with a spectroscopic device, and detecting monochromated fluorescent X-rays with an X-ray detector, which spectrometer includes the X-ray tube having a target with an element including vanadium, an X-ray filter disposed on a path of travel of X-rays between the X-ray tube and the sample and having a predetermined transmittance for V—Kα line from the X-ray tube and made of a material which is an element of which absorption edges do not exist between energies of S—Kα line and V—Kα line, and a proportional counter having a detector gas containing a neon gas or a helium gas.

According to the fourth aspect of the present invention, since the provision is made of the X-ray tube capable of generating V—Kα line having a higher energy than the exciting energy of S—Kα line, which is the analytical line of sulfur, and the X-ray filter operable to sufficiently transmit the V—Kα line and to sufficiently remove continuous X-rays corresponding to an energy of the S—Kα line from the X-ray tube having the target with an element including chromium, sulfur contained in the sample can be sufficiently excited and scattered X-rays resulting from the continuous X-rays and generated from the sample can be suppressed considerably. Also, since the provision is made of the proportional counter having the detector gas containing neon or helium, the background intensity can be minimized by removing influences brought about by an escape peak of second order line at the wavelength of the S—Kα line which is the analytical line of sulfur. Accordingly, the lower limit of detection and the precision of analysis of a very small amount concentration can be improved considerably.

In the practice of the fourth aspect of the present invention, the target of the X-ray tube may be made of a vanadium metal. The X-ray filter may be of any type provided that it has, for example, a 50% or higher transmittance for the V—Kα line and may have a thickness appropriate to a material such as, for example, aluminum, iron or vanadium foil of which absorption edges do not exist between energies of V—Kα line and S—Kα line which is the analytical lines of sulfur. The proportional counter is preferably of a type that is employed in the practice of the first aspect of the present invention.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF THE PREFERRED EMBODIMENTS

Figure 1:
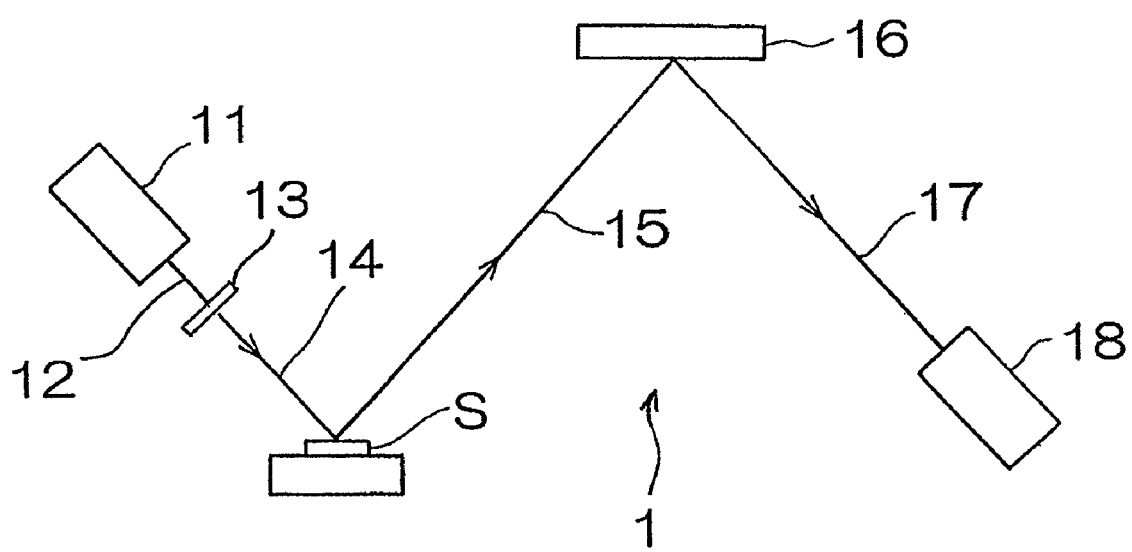
FIG. 1 is a schematic diagram showing an X-ray fluorescence spectrometer according to a first preferred embodiment of the present invention.

Hereinafter, an X-ray florescence spectrometer according to a first preferred embodiment of the present invention will be described. As shown in FIG. 1, the X-ray fluorescence spectrometer for measuring the concentration of sulfur contained in a diesel oil, which is a kind of fuel oil, includes a chromium X-ray tube 11 having a target of chromium metal, an X-ray filter 13 for transmitting 60% or more of Cr—Kα line of primary X-rays 12 emitted from the chromium X-ray tube and comprised of, for example, an aluminum foil of 12 μm in thickness, a spectroscopic device 16 for monochromating fluorescent X-rays 15 emitted from a sample S, and comprised of, for example, graphite, and a sealed proportional counter 18 filled with a detector gas of, for example, neon gas and operable to detect fluorescent X-rays 17 which have been monochromated.

Figure 2:
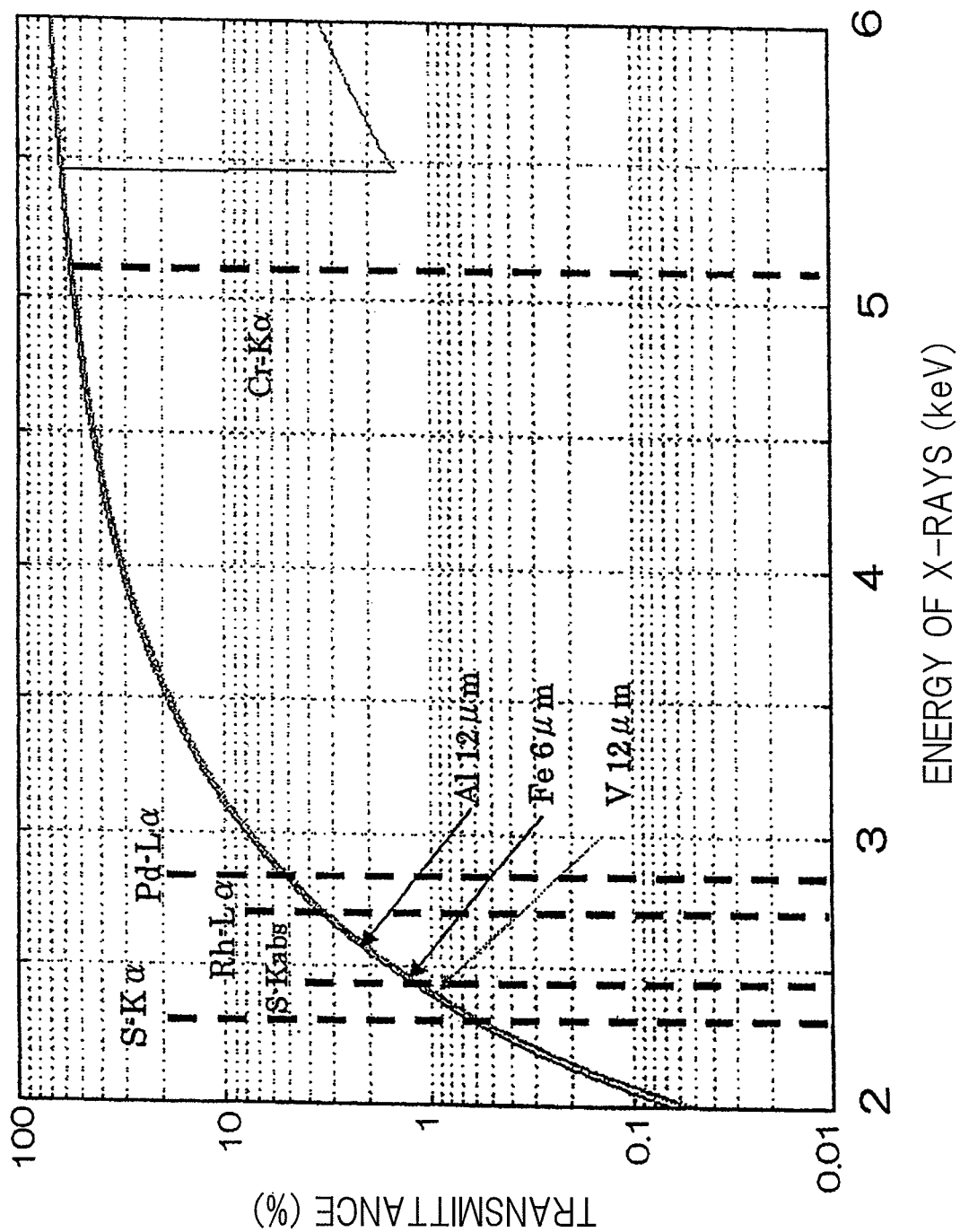
FIG. 2 illustrates respective X-ray transmittances of energies when an X-ray filter having aluminum, an X-ray filter having iron and an X-ray filter having vanadium are employed in the X-ray fluorescence spectrometer, respectively.

FIG. 2 illustrates respective X-ray transmittances of energies when an filter having aluminum of 12 μm in thickness, a filter having iron of 6 μm in thickness and a filter having vanadium of 12 μm in thickness are employed, respectively. Those filters have their respective thicknesses so that the respective transmittances of those filters remain the same. As shown in FIG. 2, 60% or more of Cr—Kα line (5.41 keV) of primary X-rays 12 emitted from a chromium X-ray tube is transmitted and the transmittance of S—Kα line, which is the analytical line, is about 0.6%. In order to sufficiently excite sulfur, which is an element to be analyzed, the X-ray filter is preferred to be of a type capable of transmitting 50% or more of the Cr—K α line. The type capable of transmitting 60% or more of the Cr—Kα line is more preferred. The X-ray filter must be made of a material of a kind having absorption edges which do not exist between the energy of S—Kα line, which is the analytical line, and the energy of Cr—Kα line.

As shown in FIG. 2, the X-ray filters made of aluminum, iron and vanadium, which satisfy the above condition, can exhibit the substantially same attenuation ratios between the energies from S—Kα line to Cr—Kα line. In order to obtain a predetermined transmittance for predetermined characteristic X-rays, it is necessary to determine the material for the X-ray filter and the thickness thereof through which the X-rays pass and, in the illustrated embodiment, an aluminum foil X-ray filter of 12 μm in thickness is employed in order to filter 60% or more of the Cr—Kα line. Accordingly, if the thickness of an aluminum foil is increased, the transmittance will become low, but if it is decreased, the transmittance will become high. Also, where iron or vanadium, both of which are other materials, is used, the foil thickness has to be selected so that it can exhibit the predetermined transmittance.

It has been well understood that the fluorescent X-rays from the sample are incident on the proportional counter and the argon gas, which is a gas in the detector, exhibits an escape peak at the value of energy, which is lower than the incident fluorescent X-rays by an energy of the Ar—Kα line and the fluorescent X-rays of high order lines such as second order line for the analytical line form interfering lines. However, it has not yet been understood that the high order lines such as the second order line of the continuous X-rays diffracted by the spectroscopic device result in an escape peak and this forms a background, resulting in error in analysis and deterioration in analytical precision, and this phenomenon has now been discovered. Accordingly, to remove the interference of the high order lines of the continuous X-rays has not been attempted before. For this reason, in the illustrated embodiment, for removing the escape peak of the high order lines of the continuous rays, the use is made of a gas filled proportional counter in which as a detector gas, a mixed gas consisting of a neon gas and a carbon dioxide gas, for example, 3% of the carbon dioxide gas is filled. Effects similar to that afforded by this gas filled proportional counter can be obtained even with a gas flow proportional counter.

If a neon gas or a helium gas is employed as the detector gas in the proportional counter, the counting efficiency of X-rays of the second order line energy of the light element, that is, X-rays of the second order line energy of sulfur is so very low that most of influences brought about by the second order line of the continuous X-rays can be eliminated and, since the escape peak generated by the neon gas or the helium gas can remove influences on the S—Kα line, which is the analytical line of sulfur, the background can be considerably reduced.

The result of analysis of 4 ppm of sulfur contained in a diesel oil, which was made with the use of the X-ray fluorescence spectrometer 1 according to the above discussed embodiment and that made with the use of the conventional X-ray fluorescence spectrometer 9 are shown in Table 2 below. The X-ray fluorescence spectrometer 1 according to the foregoing embodiment of the present invention includes a chromium X-ray tube, an aluminum foil filter having a thickness of 12 μm and a sealed proportional counter having a mixed gas of neon and carbon dioxide filled therein. On the other hand, the conventional X-ray fluorescence spectrometer 9 include a palladium X-ray tube and a sealed proportional counter having a mixed gas of argon and methane filled therein, but includes no primary beam filter. Other structural features including a spectroscopic device are identical.

As shown in Table 2, in the first embodiment of the present invention, the background is reduced down to 1/40 of the conventional embodiment, the ratio of the net intensity (the intensity calculated by subtracting the background intensity from the peak intensity) to the background intensity is improved by a factor of more than 10, and the sulfur concentration equivalent value of the background intensity is 2.0 ppm. Because of this, influences brought about by variation of the background intensity among samples could have been kept to the minimum. Also, the lower limit of detection could have been improved by a factor of 1.7. The present invention provides the spectrometer effective to satisfy not only the regulated value of the concentration of sulfur contained in the currently available fuel oil, but also the regulated value which would be required in the future.

TABLE 2

|  | Conventional Embodiment | First Embodiment | Example of Application of First Embodiment |
|---|---|---|---|
| X-ray Tube Target | Palladium | Chromium | Chromium |
| Primary Beam Filter | Not used | Aluminum 12 μm | Iron 6 μm |
| Net Intensity of 4 ppm Sulfur | 6944 | 1902 | 1908 |
| Background Intensity | 37542 | 975 | 930 |
| Sulfur Con. Equivalent of Background Intensity | 21.6 | 2.0 | 1.9 |
| Net Intensity/Background Intensity Ratio | 0.18 | 1.95 | 2.05 |
| Lower Limit of Detection | 0.33 | 0.20 | 0.19 |
| Standard Deviation ppm (at Sulfur 4 ppm) | 0.15 | 0.13 | 0.13 |

Although in the first embodiment described hereinabove, the aluminum foil of 12 μm in thickness has been shown and described as employed for the X-ray filter, the result of analysis exhibited in an example of application, in which an iron thin foil of 6 μm in thickness has been employed for the X-ray filter, is also shown in Table 2. As is the case with the aluminum filter, the background is reduced down to 1/40, the ratio of the net intensity to the background intensity is improved by a factor of more than 11, and the lower limit of detection could have been improved by a factor of 1.7. Even the X-ray filter in the form of the iron thin foil of 6 μm in thickness has a transmittance of 60% or more for the Cr—Kα line. As discussed above, it will readily be seen that similar effects can be obtained if the X-ray filter having a predetermined transmittance for the Cr—Kα lines.

Figure 3:
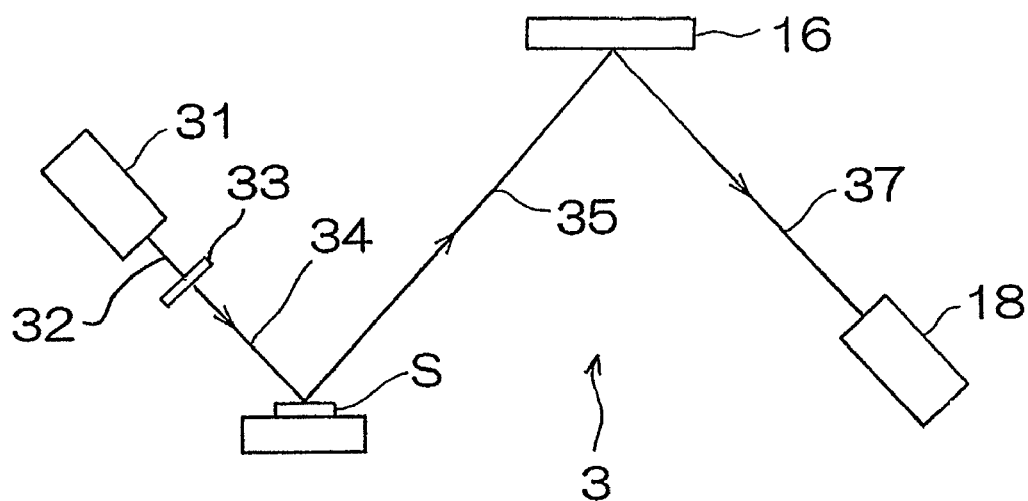
FIG. 3 is a schematic diagram showing the X-ray fluorescence spectrometer according to a second preferred embodiment of the present invention.

The X-ray fluorescence spectrometer according to a second preferred embodiment of the present invention will now be described. As shown in FIG. 3, the X-ray fluorescence spectrometer for measuring the concentration of sulfur contained in a diesel oil, which is a kind of fuel oil, in accordance with this embodiment includes a titanium X-ray tube 31 having a target of titanium metal, an X-ray filter 33 for transmitting, for example, 40% or more of Ti—Kα line of primary X-rays 32 emitted from the titanium X-ray tube 31 and comprised of, for example, a titanium thin foil of 15 μm in thickness, a spectroscopic device 16 for monochromating fluorescent X-rays 35 emitted from a sample S, and comprised of, for example, graphite, and a sealed proportional counter 18 filled with a detector gas which is, for example, a gaseous mixture of neon and carbon dioxide and operable to detect the fluorescent X-rays 37 which have been monochromated.

In order to sufficiently excite sulfur that is an element to be analyzed, the X-ray filter 33 is preferably of a type capable of transmitting 50% or more of the Ti—Kα line. By way of example, so that the X-ray filter 33 may have a 50% transmittance for the Ti—Kα line, it should have a thickness appropriate to such a material as aluminum, iron, titanium or vanadium and the predetermined characteristic X-rays in a manner similar to that discussed in connection with the aluminum X-ray filter.

In this embodiment described above, a proportional counter similar to that employed in the practice of the previously described first embodiment is employed and, therefore, effects similar to that can be obtained.

Figure 4:
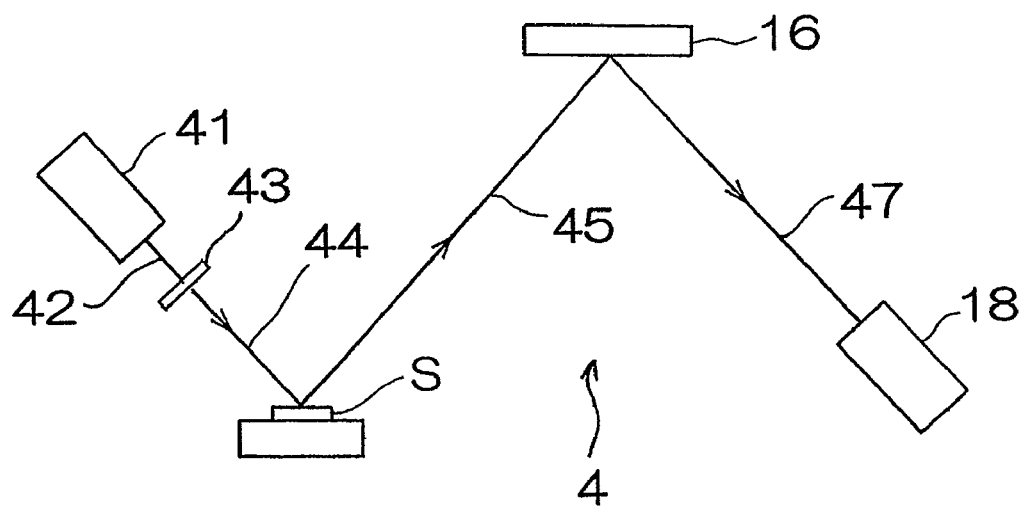
FIG. 4 is a schematic diagram showing the X-ray fluorescence spectrometer according to a third preferred embodiment of the present invention.

The X-ray fluorescence spectrometer according to a third preferred embodiment of the present invention will be described hereinafter. As shown in FIG. 4, the X-ray fluorescence spectrometer for measuring the concentration of sulfur contained in a diesel oil, which is a kind of fuel oil, in accordance with this embodiment includes a scandium X-ray tube 41 having a target of scandium metal, an X-ray filter 43 for transmitting, for example, 30% or more of Sc—Kα line of primary X-rays 42 emitted from the scandium X-ray tube 41 and comprised of, for example, a titanium thin foil of 15 μm in thickness, a spectroscopic device 16 for monochromating fluorescent X-rays 45 emitted from a sample S, and comprised of, for example, graphite, and a sealed proportional counter 18 filled with a detector gas which is, for example, a gaseous mixture of neon and carbon dioxide and operable to detect the fluorescent X-rays 47 which have been monochromated.

In order to sufficiently excite sulfur that is an element to be analyzed, the X-ray filter 43 is preferably of a type capable of transmitting, for example, 30% or more of the Sc—Kα line. By way of example, so that the X-ray filter 43 may have a 35% or higher transmittance relative to the Sc—Kα line, it should have a thickness appropriate to such a material as aluminum, iron, titanium or scandium and the predetermined characteristic X-rays in a manner similar to that discussed in connection with the aluminum X-ray filter.

In this embodiment described above, a proportional counter similar to that employed in the practice of the previously described first embodiment is employed and, therefore, effects similar to that can be obtained.

Figure 5:
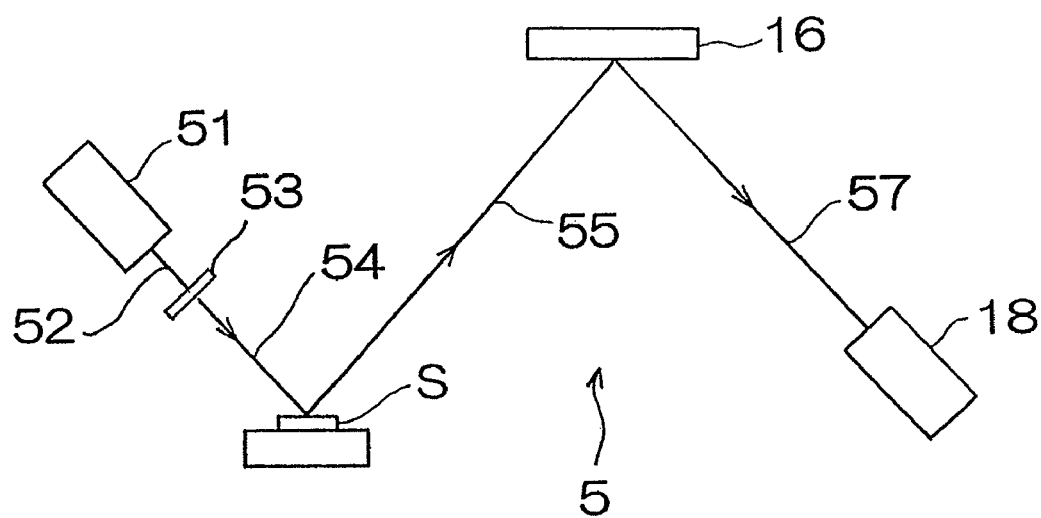
FIG. 5 is a schematic diagram showing the X-ray fluorescence spectrometer according to a fourth preferred embodiment of the present invention.
Figure 6:
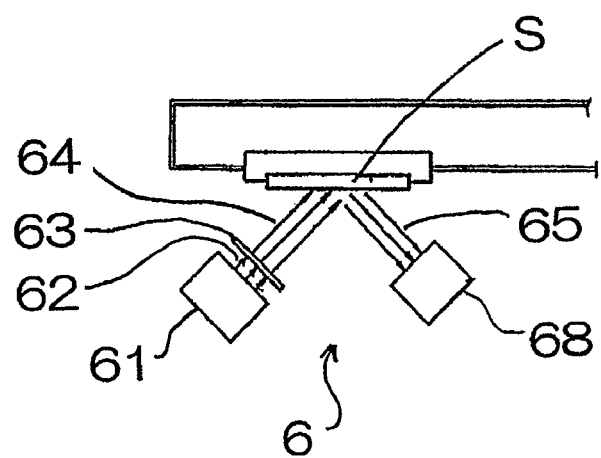
FIG. 6 is a schematic diagram showing the conventional energy dispersive X-ray fluorescence spectrometer.
Figure 7:
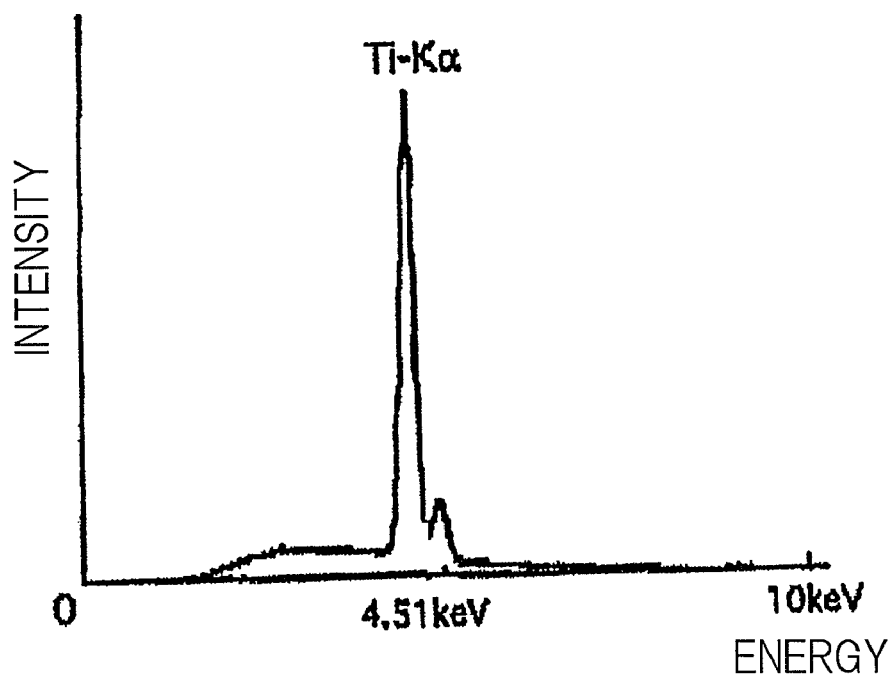
FIG. 7 illustrates a spectrum of primary X-rays emitted from a titanium X-ray tube employed in the conventional X-ray fluorescence spectrometer.
Figure 8:
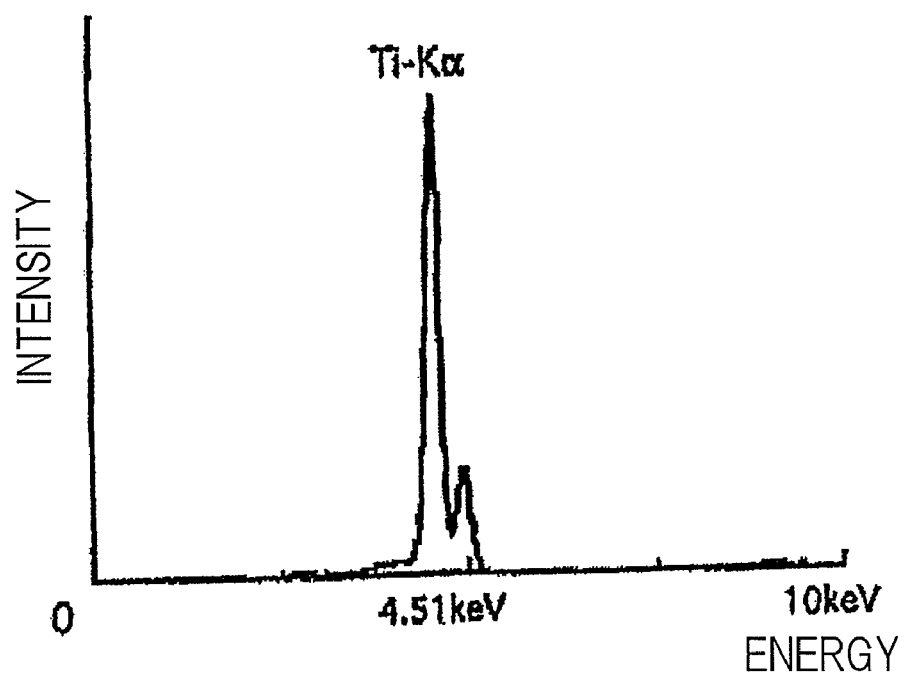
FIG. 8 is illustrates a spectrum of the primary X-rays emitted from a titanium X-ray tube employed in the conventional X-ray fluorescence spectrometer, which is exhibited after filtration through a titanium X-ray filter.
Figure 9:
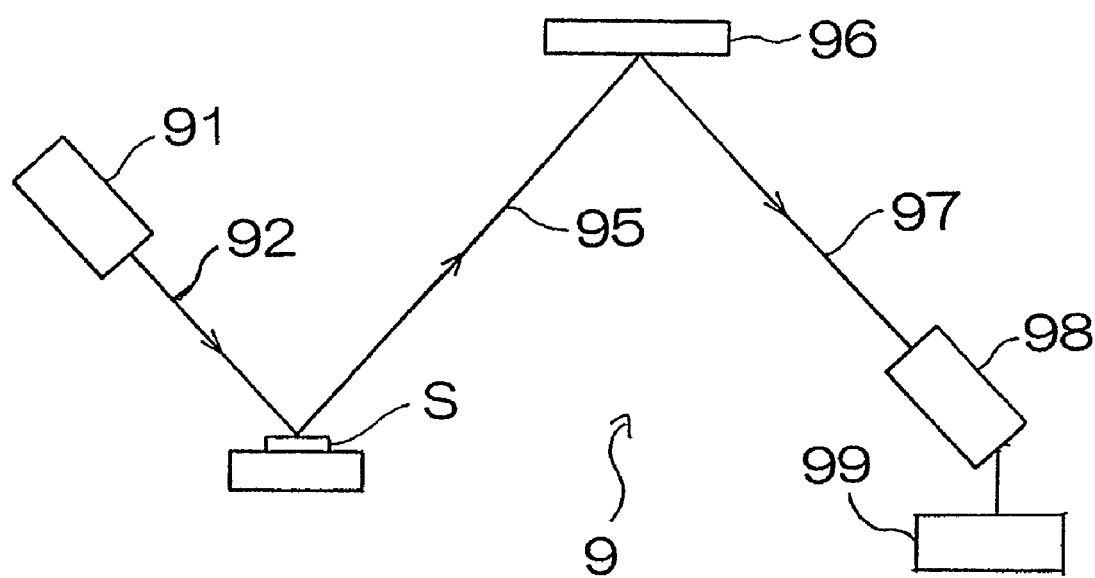
FIG. 9 is a schematic diagram showing the conventional wavelength dispersive X-ray fluorescence spectrometer.

The X-ray fluorescence spectrometer according to a fourth preferred embodiment of the present invention will be described hereinafter. As shown in FIG. 5, the X-ray fluorescence spectrometer for measuring the concentration of sulfur contained in a diesel oil, which is a kind of fuel oil, in accordance with this embodiment includes a vanadium X-ray tube 51 having a target of vanadium metal, an X-ray filter 53 for transmitting, for example, 50% or more of V—Kα line of primary X-rays 52 emitted from the vanadium X-ray tube 51 and comprised of, for example, a vanadium thin foil of 12 μm in thickness, a spectroscopic device 16 for monochromating fluorescent X-rays 55 emitted from a sample S, and comprised of, for example, graphite, and a sealed proportional counter 18 filled with a detector gas which is, for example, a gaseous mixture of neon and carbon dioxide and operable to detect the fluorescent X-rays 57 which have been monochromated.

In order to sufficiently excite sulfur that is an element to be analyzed, the X-ray filter 53 is preferably of a type capable of transmitting 50% or more of the V—Kα line. By way of example, so that the X-ray filter 53 may have a 50% transmittance for the V—Kα line, it should have a thickness appropriate to such a material as aluminum, iron or vanadium and the predetermined characteristic X-rays in a manner similar to that discussed in connection with the aluminum X-ray filter.

In this embodiment described above, a proportional counter similar to that employed in the practice of the previously described first embodiment is employed and, therefore, effects similar to that can be obtained.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention.

Accordingly, such changes and modifications are, unless they depart from the scope of the present invention as delivered from the claims annexed hereto, to be construed as included therein.

What is claimed is:

1. An X-ray fluorescence spectrometer for measuring the concentration of sulfur contained in a sample, by irradiating the sample with primary X-rays from an X-ray tube, monochromating fluorescent X-rays emitted from the sample with a spectroscopic device, and detecting monochromated fluorescent X-rays with an X-ray detector, which spectrometer comprises:

the X-ray tube having a target including chromium;

an X-ray filter disposed on a path of travel of X-rays between the X-ray tube and the sample and having a predetermined transmittance for Cr—K$\alpha$ line from the X-ray tube and made of a material which is an element of which absorption edges do not exist between energies of S—K$\alpha$ line and Cr—K$\alpha$ line; and a proportional counter having a detector gas containing a neon gas or a helium gas.

2. An X-ray fluorescence spectrometer for measuring the concentration of sulfur contained in a sample, by irradiating the sample with primary X-rays from an X-ray tube, monochromating fluorescent X-rays emitted from the sample with a spectroscopic device, and detecting monochromated fluorescent X-rays with an X-ray detector, which spectrometer comprises:

the X-ray tube having a target including titanium;

an X-ray filter disposed on a path of travel of X-rays between the X-ray tube and the sample and having a predetermined transmittance for Ti—K$\alpha$ line from the X-ray tube and made of a material which is an element of which absorption edges do not exist between energies of S—K$\alpha$ line and Ti—K$\alpha$ line; and a proportional counter having a detector gas containing a neon gas.

3. An X-ray fluorescence spectrometer for measuring the concentration of sulfur contained in a sample, by irradiating the sample with primary X-rays from an X-ray tube, monochromating fluorescent X-rays emitted from the sample with a spectroscopic device, and detecting monochromated fluorescent X-rays with an X-ray detector, which spectrometer comprises:

the X-ray tube having a target including scandium;

an X-ray filter disposed on a path of travel of X-rays between the X-ray tube and the sample and having a predetermined transmittance for Sc—K$\alpha$ line from the X-ray tube and made of a material which is an element of which absorption edges do not exist between energies of S—K$\alpha$ line and Sc—K$\alpha$ line; and a proportional counter having a detector gas containing a neon gas.

4. An X-ray fluorescence spectrometer for measuring the concentration of sulfur contained in a sample, by irradiating the sample with primary X-rays from an X-ray tube, monochromating fluorescent X-rays emitted from the sample with a spectroscopic device, and detecting monochromated fluorescent X-rays with an X-ray detector, which spectrometer comprises:

the X-ray tube having a target including vanadium;

an X-ray filter disposed on a path of travel of X-rays between the X-ray tube and the sample and having a predetermined transmittance for V—K$\alpha$ line from the X-ray tube and made of a material which is an element of which absorption edges do not exist between energies of S—K$\alpha$ line and V—K$\alpha$ line; and a proportional counter having a detector gas containing a neon gas.

* * * * *

UNITED STATES PATENT AND TRADEMARK OFFICE
CERTIFICATE OF CORRECTION

PATENT NO. : 7,949,093 B2  
APPLICATION NO. : 12/296383  
DATED : May 24, 2011  
INVENTOR(S) : Yoshiyuki Kataoka et al.

It is certified that error appears in the above-identified patent and that said Letters Patent is hereby corrected as shown below:

On the title page, item [73] Assignee: Delete "RIGAKU INDUSTRIAL CORPORATION" and insert --RIGAKU CORPORATION--

Signed and Sealed this  
Twenty-sixth Day of July, 2011

David J. Kappos  
*Director of the United States Patent and Trademark Office*